United States Patent
Miyagi et al.

(12)

(10) Patent No.: US 6,225,454 B1
(45) Date of Patent: May 1, 2001

(54) SIALIDASE LOCALIZED IN PLASMA MEMBRANE AND DNA CODING FOR THE SAME

(75) Inventors: Taeko Miyagi; Tadashi Wada; Yuko Yoshikawa, all of Natori (JP)

(73) Assignee: Miyagi Ken (JP)

( * ) Notice: Subject to any disclaimer, the term of this patent is extended or adjusted under 35 U.S.C. 154(b) by 0 days.

(21) Appl. No.: 09/423,340

(22) PCT Filed: May 11, 1998

(86) PCT No.: PCT/JP98/02072

§ 371 Date: Nov. 22, 1999

§ 102(e) Date: Nov. 22, 1999

(87) PCT Pub. No.: WO98/53052

PCT Pub. Date: Nov. 26, 1998

(30) Foreign Application Priority Data

May 22, 1997 (JP) .................................................. 9-132174

(51) Int. Cl.$^7$ .................................................. C07H 21/04
(52) U.S. Cl. .................... 536/23.2; 424/94.1; 424/94.61; 424/520; 435/183; 530/300; 530/350; 536/23.5
(58) Field of Search ................................ 424/94.1, 94.61, 424/520; 435/183, 206–210; 530/300, 350; 536/23.2, 23.5

(56) References Cited

PUBLICATIONS

Ferrari, J. et al., "Cloning and expression of a soluble sialidase from Chinese hamster ovary cells: sequence alignment similarities to bacterial sialidases", Glycobiology vol. 4, No. 3, pp. 367–373, (1994).

Miyagi, T. et al., "Molecular Cloning and Expression of cDNA Encoding Rat Skeletal Muscle Cytosolic Sialidase", J. Biol. Chem. 268, pp. 26435–26440, (1993).

Miyagi, T. et al., "Biochemical and Immunological Studies on Two Distinct Ganglioside–Hydrolyzing Sialidases from the Particulate Fraction of Rat Brain", J. Biochem. 107, pp. 787–793, (1990).

Miyagi, T. et al., "Rat–liver lysosomal sialidase: Solubilization, substrate specificity and comparison with the cytosolic sialidase", Eur. J. Biochem. 141, pp. 75–81, (1984).

Miyagi, T. et al., "Purification And Characterization Of Cytosolic Sialidase From Rat Liver", J. Biol. Chem. vol. 260, No. 11, pp. 6710–6716, (1985).

Miyagi, T., "The Variety and the Significance of Animal Sialidases, " Seikagaku (Biochemistry), vol. 62, No. 12, pp. 1506–1512, (1990) (abstract provided in English).

Miyagi, T. et al., "The Analysis of the Chracteristics and Function of Sialidases, which Hydrolyzes Gangliosides, " Shishitsu Seikagaku Kenkyu (The Research of Lipid Biochemistry), vol. 36, pp. 259–262 (1994) (partial translation provided).

Miyagi et al.; Molecular cloning and expression of cDNA encoding rat skeletal muscle cytosolic sialidase. The Journal of Biological Chemistry. vol. 268 (1993) p. 26435–26440.*

* cited by examiner

Primary Examiner—Jeffrey Stucker
Assistant Examiner—Ulrike Winkler
(74) Attorney, Agent, or Firm—Kilpatrick Stockton LLP

(57) ABSTRACT

Sialidases localized on plasma membranes having the amino acid sequence of SEQ ID NO: 2 or SEQ ID NO: 4 and DNA coding for the sialidase having the nucleotide sequence of SEQ ID NO: 1 or SEQ ID NO: 3.

10 Claims, 2 Drawing Sheets

| Peptide | Amino acid sequence | Sense primer | Antisense primer |
|---------|---------------------|--------------|------------------|
| DN1-1 | DAEILSHVQg RGYS (SEQ ID NO 5) | GAYGCIGARATYCTIWIICAYGTICA (SEQ ID NO 10) | CCCTGIACRT GIIWIAGRAT TYCIGCRTC (SEQ ID NO 11) |
| | | | CCCTGIACRT GIIWISIRTA ICCICIRTC (SEQ ID NO 13) |
| DN-2 | DdlgA (SEQ ID NO 6) | GAYIGIGGIT AYISIWIICA YGTICAGGG (SEQ ID NO 12) | GCICCIAGRT CRTC (SEQ ID NO 15) |
| DN-3 | EEVtS (SEQ ID NO 7) | GAYGAYCTIG GIGC (SEQ ID NO 14) | ISIIGTIACY TCYTC (SEQ ID NO 16) |
| AP-1 | (K)yeel (SEQ IO NO 8) | | IAIYTCYTCR TAYTT (SEQ ID NO 17) |
| AP-3 | (K)DEDAlhlv (SEQ ID NO 9) | AARGAYGARG AYGCICTICA YCTIGT (SEQ ID NO 18) | ACIAGRTGIA GIGCRTCYTC RTC (SEQ ID NO 19) |

Fig. 1

```
 49'                                   KDEDALHLVLRRG--L                   BBmSD

**.* .*****

1" METCPVLQKETLFHTEVYAYRIPALLYLKKQKTLLAFAEKRASRTDEHAELIVLRRGSYN         RMcSD

63' RTGQSVQWEPLKSLMKATLPGHRTMNPCPVWERKSGYVYLFFICVQGHVTERQQIMSGRN         BBmSD

... *.*.*  .  . .* *  ***.*****......  ..**** *.*.*.*...*. . *

61" GATNHVKWQPEEVVTQAQLEGHRSMNPCPLYDKQTKTLFLFFIAVPGRVSEQHQLQTRVN         RMcSD

123' AARLCFICSQDAGHSWSDVRDLTEEVIGPEVTHWATFAVGPGHGIQL--QSGRLIIPAYA         BBmSD

..***  .  *  *  * .** *.****..**.. .**********. **  ..*.*..****

121" VTRLCRVTSTDYGMNWSPVQDLTETTIGSTHQDWATFAVGPGHCLQLRNRAGSLLVPAYA         RMcSD

181' YYIPFWFFCFRLPYRARPHSLMIYSDDLG                                       BBmSD

*

181" YRKLHPVHKPTPFAFCFISLDHGHTWELGNFVSENSLECQVAEVGTGAHRVVYLNARSFI        RMcSD
```

Fig. 2

SIALIDASE LOCALIZED IN PLASMA MEMBRANE AND DNA CODING FOR THE SAME

This application is a national stage PCT/J98/02072, filed May 11, 1998.

TECHNICAL FIELD

The present invention provides a novel sialidase and DNA coding for it. More precisely, the present invention provides sialidase that localizes in plasma membrane, and specifically hydrolyzes gangliosides, and DNA coding for it.

The sialidase of the present invention and the DNA coding for it are expected to be utilized as a reagent used for saccharide chain studies and a medicament used for gene diagnosis and gene therapy.

BACKGROUND ART

Sialidase is a glycohydrolytic enzyme present in living bodies, which eliminates a sialic acid residue from a non-reducing terminal of saccharide chains of glycoproteins or glycolipids. It has been known that, when sialic acid is removed from saccharide chain molecules, not only the degradation of these molecules begins, but also molecular conformation and many of important cell functions such as recognition mechanism by receptors, cell adhesion, and immunomechanism may be changed. It has also become clear that sialidase exhibits rapid activity change in connection with proliferation and canceration of cells, and it is involved in the metastatic ability of cancer cells. However, there is little knowledge about how sialic acid is eliminated in vivo. This is because the studies of mammalian sialidases on the molecular level are behindhand, and hence there are many unknown points concerning their structures and expression mechanism.

Because mammalian sialidase exhibits only low activity, and is extremely unstable, isolation and purification of the enzyme have been difficult. Sialidase has been often considered for a long time to be one of the mere lysosomal enzymes involved in the dissimilation and degradation. Under such a situation, we isolated and purified the enzyme by using mainly rat tissues as the source of the enzyme, and found that there were four types of sialidases which differ from sialidases of bacteria, viruses, protozoa and the like in their natures (Miyagi, T. and Tsuiki, S., *Eur. J. Biochem.* 141, 75–81, 1984; Miyagi, T. et al., *J. Biochem.* 107, 787–793, 1990; Miyagi, T. and Tsuiki, S., *J. Biol. Chem.* 260, 6710–6716, 1985). These enzymes each localize in lysosomal matrix, lysosome membrane, plasma membrane (cell surface membrane), and cytoplasm within a cell, respectively, and they are different from each other not only in enzymological characteristics such as substrate specificity, but also in immunological properties. Among those sialidases, the sialidase localized in cytoplasm can be obtained as a homogenous purified product from rat skeletal muscles. Its cDNA cloning has been succeeded for the first time in the world as for animal sialidases, and its primary structure has been determined (Miyagi T. et al., *J. Biol. Chem.*, 268, 26435–26440, 1993). Its genomic structure analysis has also been done, and as for its function, it has been elucidated that the enzyme participates in the differentiation and the growth of skeletal muscle cells by using the cDNA as a probe. These studies can be considered a part of pioneer researches in sialidase studies in the world.

By the previous studies, it has become clear that there is possibility that the sialidase localized in plasma membrane exhibits activity elevation upon proliferation and canceration of cells, and it is also deeply concerned with the differentiation of nerve cells and the signal transduction of cells. To date, however, it has not been understood at all about the structure of this enzyme, the mechanism causing the activity change and the like. In order to answer these questions, what many researchers in this field have long been desired is cloning of its cDNA. For example, if the mechanism of cancerous change due to this enzyme could be elucidated, it would be possible to utilize the results in diagnosis and therapy of cancers. Further, because gangliosides exist in surface membranes of many cells and participate in important cell functions such as cell adhesion and informational communication, and they are also main cerebral components, the sialidase utilizing them as a specific substrate is estimated to be involved in certain important cranial nerve functions.

SUMMARY OF THE INVENTION

The present invention has been accomplished in view of the aforementioned present condition. An object of the present invention is to provide the sialidase localized in plasma membrane and DNA that codes for it.

The inventors of the present invention earnestly conducted studies in order to achieve the aforementioned object, and as a result, succeeded in isolating the sialidase localized in plasma membrane and cloning of cDNA coding for it. Furthermore, they found that the aforementioned sialidase was unique in that it substantially specifically hydrolyzed gangliosides (glycolipids containing sialic acid), which are substrates that similarly localize mainly in plasma membrane, and it was completely different from other mammalian sialidases and microbial sialidases in enzymatic substrate specificity. Thus, they accomplished the present invention.

That is, the present invention provides a protein defined in the following (A) or (B):

(A) a protein which has the amino acid sequence of SEQ ID NO: 2 or SEQ ID NO: 4, or (B) a protein which has the amino acid sequence including substitution, deletion, insertion, or transition of one or several amino acid residues in SEQ ID NO: 2 or SEQ ID NO: 4, and exhibits activity to eliminate a sialic acid residue from a non-reducing terminal of ganglioside.

The present invention also provides DNA coding for the protein defined in the above (A) or (B). Specifically, such DNA may be DNA which has the nucleotide sequence of SEQ ID NO: 1 or SEQ ID NO: 3.

A sialidase which has the aforementioned characteristics will be referred to as the "sialidase of the present invention" hereinafter, and DNA coding for it will be referred to as the "DNA of the present invention" hereinafter.

Hereafter, the present invention will be explained in detail.

<1> Sialidase of the Present Invention

The sialidase of the present invention is a protein which has the amino acid sequence of SEQ ID NO: 2 or SEQ ID NO: 4. Moreover, the sialidase of the present invention include a protein which has the amino acid sequence including substitution, deletion, insertion, or transition of one or several amino acid residues in SEQ ID NO: 2 or SEQ ID NO: 4, so long as it exhibits activity for eliminating a sialic acid residue from a non-reducing terminal of ganglioside.

Among the aforementioned sialidases, the sialidase that has the amino acid sequence of SEQ ID NO: 2 has the following physicochemical properties.

(1) Activity

It eliminates sialic acid residues from a non-reducing terminal of ganglioside.

(2) Substrate Specificity

It acts on gangliosides, but not act on glycoproteins and oligosaccharides. Specifically, it acts on GD3-ganglioside, GD1a-ganglioside, GM3-ganglioside, and synthetic gangliosides (GSC-17($\alpha$2-3) and GSC-61($\alpha$2-6)), but it does not substantially act on GM2-ganglioside, GM1-ganglioside, orosomucoid, fetuin, glycophorin, ovine submaxillary gland mucin, and bovine submaxillary gland mucin. It weakly acts on $\alpha$2-3 sialyllactose, and 4-MUNeuAc (4-methylumbelliferyl N-acetylneuraminic acid).

(3) Optimum pH 4.7 to 5.0

(4) Molecular Weight

About 65,000 as determined by sucrose density gradient centrifugation,

About 52,000 as determined by SDS-polyacrylamide gel electrophoresis under reducing condition (5) Inhibition and Activation A surface active agent is required for the activity. For example, it is highly active in the presence of 0.1 to 0.2% of Triton X-100.

It is strongly inhibited by heavy metal ions such as $Cu^{2+}$, and 4-hydroxy mercury benzoate.

It is stabilized by dithiothreitol, Neu5Ac2en (2-deoxy-2,3-dehydro-N-acetylneuraminic acid), and glycerol. However, it is weakly inhibited by Neu5Ac2en.

Among the sialidases of the present invention, the sialidase which has the aforementioned characteristics is an enzyme derived from bovine, whereas the sialidase which has the amino acid sequence of SEQ ID NO: 4 in one derived from human. These exhibit 82% homology in their amino acid sequences, and they have a transmembrane domain, glycosylation site, and Asp-box, which is a consensus sequence of sialidase, at the same locations. Therefore, the enzyme derived from human is considered to have the same physicochemical properties as the enzyme derived from bovine.

The sialidase of the present invention can be obtained from a bovine brain, for example, as follows. All of the following procedures are preferably carried out at a low temperature.

A bovine brain is homogenized in a buffer, and centrifuged at 1000×g for 10 minute, and the supernatant is further centrifuged at 30,000×g for 1 hour. After the centrifugation, the precipitate fraction is suspended in a buffer, added 5% deoxycholic acid, sufficiently homogenized, and centrifuged at 100,000×g for one hour to obtain a soluble fraction as a supernatant. The buffer preferably contains an inhibitor for proteases, dithiothreitol, surface active agent and the like.

The above soluble fraction is applied to a DEAE-cellulose column and, after the column is washed, eluted with a buffer containing 0.2 M NaCl for fractionation. A fraction exhibiting the sialidase activity is dialyzed against a buffer, then applied on Octyl-Sepharose, and separated by elution with a linear gradient of 0.1–0.4% Triton X-100.

Then, an active fraction is applied to Heparin-Sepharose (Pharmacia), washed with a buffer containing 0.25 M NaCl, and eluted with a 0.2–1 M NaCl linear gradient to concentrate the active fraction. The above concentrated enzyme solution is loaded on Sephacryl S-200 (Pharmacia), and separated by elution with a buffer containing 0.02 mM NeuAc2en (2-deoxy-2,3-dehydro-N-acetylneuraminic acid).

The obtained active fraction is diluted to have a Triton X-100 concentration of 0.02%, added to RCA-lectin agarose (Pharmacia), washed with a buffer containing 0.02% Triton X-100, and eluted with a buffer containing 0.2 M lactose. This active fraction is loaded on a MonoQ (Pharmacia) column, and eluted with a 0–0.5 M NaCl linear gradient.

The active fraction is loaded on an activated thiol Sepharose (Pharmacia) column, washed with a 0.15 M NaCl buffer containing 10% glycerol, and then with 0.5 M NaCl buffer containing 10% glycerol, and eluted with 0.05 M NaCl buffer containing 0.05 M dithiothreitol. The active fraction is concentrated in a MonoQ column.

The above concentrate is loaded on an affinity column utilizing a synthetic ganglioside GM3 [GSC-211, NeuAc-Gal-Glc-O(CH$_2$)$_8$NH$_2$] as a ligand (Hasegawa A. et al. J. Carbohydr. Chem., 9, 201–214, 1990), and separated by elution with a 0–0.5 M NaCl gradient. The affinity column can be obtained by allowing GSC-211 to couple with ECH-Sepharose (Pharmacia) in the presence of N-ethyl-N'-(3'-dimethyl-aminopropyl)carbodiimide hydrochloride.

The sialidase enzyme is purified as described above as a protein having a molecular weight of 52 kD as determined by SDS-polyacrylamide gel electrophoresis.

Further, since DNA coding for the sialidase of the present invention has been obtained, the sialidase of the present invention can also be obtained by expressing the DNA in a suitable host-vector system. As for the host-vector system, a cultured cell can be used as a host, and a vector suitable for this host can be used. Materials and methods therefore may be those usually used for the production of heterogenous proteins utilizing genetic recombination techniques. When DNA coding for the sialidase of the present invention is ligated to a vector, a vector containing sequences required for regulation of gene expression such as promoter and terminator that can be expressed in the host as required may be used.

<2> DNA of the Present Invention

Because the amino acid sequence of the protein encoded by the DNA of the present invention has been elucidated, the DNA of the present invention can be cloned based on the amino acid sequence. In the examples mentioned below, a partial amino acid sequence of the sialidase of the present invention is determined, oligonucleotide primers are synthesized based on the partial amino acid sequence, and the DNA of the present invention is obtained from a bovine brain cDNA library by PCR (polymerase chain reaction) using the oligonucleotides primers.

Although the sequence of the DNA of the present invention is not particularly limited so long as it codes for the amino acid sequence of SEQ ID NO: 2 or 4, the nucleotide sequences of SEQ ID NOS: 1 and 3 can be specifically mentioned. Further, existence of sialidases having the amino acid sequence of SEQ ID NO: 2 or SEQ ID NO: 4 including substitution, deletion, insertion, or transition of one or several amino acid residues, and genes coding for them is expected due to difference of animal species, individuals or varieties. Such DNA coding for the substantially same protein as the sialidase of the present invention also falls within the scope of the DNA of the present invention. Such DNA can also be obtained from a cell harboring it by hybridizing it with the nucleotide sequence of SEQ ID NO: 1 or 3 or a part thereof under a stringent condition, and isolating DNA coding for a protein which has sialidase activity. DNA coding for a sialidase having such a mutation as mentioned above may also be obtained by, for example, site-specific mutagenesis or mutagenic treatment.

The term "one or several" amino acid residues means 1–80, preferably 1–30, more preferably 1–5 amino acid residues.

<3> Pregressive Applications of the Sialidase of the Present Invention and DNA Coding for It
(1) Because the sialidase of the present invention exhibits substrate specificity unique in that it substantially specifically hydrolyze gangliosides, a recombinant having the enzyme or DNA coding for the enzyme has much possibility for use as a reagent for saccharide chain studies.
(2) As one of the means for normalizing abnormality of this enzyme observed in cancer cells, for example, antisense therapy, which is a kind of gene therapy, will be expected in future. The gene structure clarified by the present invention is the important information for it. Moreover, if the expression mechanism of this enzyme becomes clear by genome structure analysis utilizing the cDNA as a probe, it will also become possible to normalize the abnormality of the expression of this enzyme in cancer and the like.
(3) Because of two reasons, i.e., the characteristic that the enzyme specifically decomposes gangliosides that are main components of brain, and its involvement in differentiation of nerve cells, the abnormalities of this enzyme may be found in certain brain diseases. In such a case, the information about the gene may be much utilized for development of gene therapy and medicaments.

BRIEF DESCRIPTION OF THE DRAWINGS

FIG. 1 represents the amino acid sequences of peptides obtained by endoproteinase digestion and lysyl endopeptidase digestion. The amino acids represented with minor characters in the figure are amino acids of low determinancy. A Lys residue presumed to have bound to the N-terminus amino acid is represented with (K).

FIG. 2 represents alignment of deduced amino acid sequences of a PCR product (BBmSD) obtained by using bovine brain cDNA as a template and a rat skeletal muscle cytoplasmic sialidase (RMcSD). Common amino acids are represented with dots ".", and analogous amino acids are represented with asterisks "*". The highly homologous regions used for the preparation of a probe are underlined.

BEST MODE FOR CARRYING OUT THE INVENTION

Hereafter, the present invention will be explained more specifically with reference to the following examples.
<1> Purification of Sialidase Localized in Plasma Membrane
(1) Method for Measuring Sialidase Activity In this example, sialidase activity was measured as follows.

A reaction system (0.2 ml) contained 50–100 nmol of sialic acid-bound saccharide substrate, 0.2 mg of bovine serum albumin, 15 mmol of sodium acetate buffer (pH 4.6), 0.2 mg of Triton X-100, and an enzyme fraction, and a substrate consisting mainly of bovine brain mixed gangliosides (Sigma, Type II) was used.

A reaction mixture having the aforementioned composition was incubated at 37° C. for 15–60 minutes, and the reaction was stopped by quick freezing. The released sialic acid was quantitated by the thiobarbituric acid method of Warren (Warren L., *J. Biol. Chem.* 234, 1971–1975, 1959) at 549 nm and 532 nm. In Steps 1, 2, and 7 explained below, the quantitation was performed by the same method after the reaction product was passed through an AGX-2 ion exchange mini column. The amount of the sialic acid (nmol) released per hour was defined as 1 unit. When a synthetic substrate, 4-methylumbelliferyl N-acetylneuraminic acid (4MU-NeuAc) was used as the sialic acid-bound saccharide substrate, Triton X-100 was excluded from the reaction system, and released 4-methylumbelliferone was quantitated by a fluorospectrophotometer.

In this example, the amount of enzyme protein was measured by the Bradford method (a kit of Biorad Co. was used), or the BCA method (Piece Chemical Co.). Further details of the measuring methods are found in the previous report (Miyagi and Tsuiki, *J. Biol. Chem.* 260, 6710–6716, 1985).

(2) Solubilization and Purification of Bovine Membrane-bound Sialidase

The whole procedure described below was carried out at 4° C. Bovine brains obtained from a slaughterhouse were freezed at −80° C. until they were used.

200 g of bovine brain was added 9 volumes of 0.32 M sucrose, 1 mM DTT (dithiothreitol), 1 mM EDTA, and 0.1 mM PMSF (phenylmethylsulfonyl fluoride), homogenized by a glass Teflon homogenizer, and centrifuged at 1000×g for 10 minute. The resulting supernatant was further centrifuged at 30,000×g for 1 hour. After the centrifucation, the resulting precipitate fraction (Step 1) was suspended in Buffer A (20 mM potassium phosphate, pH 6.8, 0.1% Triton X-100, 1 mM EDTA, 1 mM DTT) containing 180 ml of 0.1 mM PMSF, then added 5% deoxycholic acid, sufficiently homogenized, and centrifuged at 100,000×g for one hour to obtain a supernatant as a soluble fraction (Step 2).

The soluble fraction was applied to a DEAE-cellulose column (4.5×20 cm) equilibrated with Buffer A, washed, and eluted with Buffer A containing 0.2 M NaCl to collect 15 ml-fractions (Step 3). The active fraction was dialyzed against Buffer A, then applied to an Octyl-Sepharose column (2.5×7 cm) equilibrated with the same buffer, and eluted with a linear gradient (400 ml) of 0.1–0.4% Triton X-100 to collect 10-ml fractions (Step 4).

Then, the active fraction was applied to a Heparin-Sepharose column (1.5×1 cm), washed with Buffer A containing 0.25 M NaCl, and eluted with a 0.2–1 M NaCl linear gradient (200 ml) in Buffer A, and the active fraction was concentrated by ultrafiltration using a YM-10 membrane (Step 5).

Concentrated enzyme solution obtained from 3 times of the elution from the Heparin-Sepharose column was loaded on a Sephacryl S-200 column (Pharmacia, 1.5×2.5 cm.), and eluted with Buffer B (20 mM potassium phosphate, pH 6.8, 0.04% Triton X-100, 1 mM EDTA, 1 mM DTT, 0.02 mM NeuAc2en [2-deoxy-2,3-dehydro-N-acetylneuraminic acid]) at a flow rate of 10 ml/h to collect 2-ml fractions (Step 6).

The active fraction from Step 6, which was diluted so that it should have a Triton X-100 concentration of 0.02%, was applied to an RCA-lectin agarose column (1.5×2.5 cm) equilibrated with Buffer B in which only the concentration of Triton X-100 was changed to 0.02%, washed with the same buffer, and eluted with Buffer B containing 0.2 M lactose (Step 7). This active fraction was applied to a MonoQ (HR 5/5) column (Pharmacia), eluted with a 0–0.5 M NaCl linear gradient in Buffer B, and stored at −20° C. (Step 8).

The fraction obtained from 3 times of the elution in Step 8 (corresponding to 1.8 kg of the starting material) was loaded on an activated thiol-Sepharose column (Pharmacia, 1.5×2 cm), and eluted with Buffer B containing 0.15 M NaCl and 10% glycerol, and then with Buffer B containing 0.5 M NaCl and 10% glycerol, and eluted with Buffer B containing 0.5 M NaCl and DTT at a concentration raised to 50 mM. The active fraction was concentrated with a MonoQ column as in Step 8 (Step 9).

Finally, affinity column chromatography utilizing a synthetic ganglioside GM3 [GSC-211, NeuAc-Gal-Glc-O(CH$_2$)$_8$NH$_2$] (Hasegawa A. et al., *J. Carbohydr. Chem.*, 9, 201–214, 1990) as a ligand was performed. An affinity column (0.7×3 cm) was prepared by allowing the GSC-211 to couple to ECH-Sepharose (Pharmacia) in the presence of N-ethyl-N'-(3'-dimethyl-aminopropyl)carbodiimide hydrochloride according to the instruction of the manufacturer. The enzyme fraction obtained from Step 8 was loaded on the column equilibrated with Buffer C (10 mM potassium phosphate, pH 6.8, 0.04% Triton X-100, 1 mM EDTA, 1 mM DTT, 20% glycerol), and eluted with a 0–0.5 M NaCl concentration gradient in Buffer C to collect 1.5 ml-fractions (Step 10).

The purification process using 3.5 kg of bovine brains as the start material was summarized in Table 1. By the procedure explained above, the sialidase activity was purified by more than 100,000 times from the bovine brain particulate fraction. The final sample was subjected to SDS-polyacrylamide gel electrophoresis according to the method of Laemmli (Laemmli, U.K. *Nature*, 227, 680–685, 1970) to determine its purity. As a result, while a weak band at 50k was observed other than the main 52k protein band, the staining density of the 52k protein was parallel with the activity elution pattern from the affinity column, and in addition, this band was concentrated from Step 9 to 10. Therefore, it was considered to be a sialidase enzyme protein.

TABLE 1

| Step | Total amount of proteins (mg) | Total activity (Unit) | Specific activity (Unit/mg) | Purification degree (-fold) | Yield (%) |
|---|---|---|---|---|---|
| Particulate fraction | 36622 | 1666327 | 45.5 | 1 | 100 |
| Solubilized fraction | 23057 | 1616337 | 70.1 | 1.5 | 97 |
| DEAE-cellulose | 13440 | 1051740 | 78.3 | 1.7 | 63 |
| Octyl-cellulose | 1581 | 486000 | 307 | 6.7 | 29 |
| Heparin-Sepharose | 112 | 245520 | 2188 | 48 | 15 |
| Sephacryl S-200 | 4.51 | 44670 | 9926 | 218 | 2.6 |
| RCA-lectin agarose | 0.521 | 25771 | 49464 | 1087 | 1.5 |
| Mono Q | 0.220 | 19590 | 89045 | 1957 | 1.2 |
| Activated-thiol Sepharose | 0.0103 | 18660 | 1811650 | 39816 | 1.1 |
| Ganglioside-Sepharose | 0.0012 | 5773 | 4851260 | 106621 | 0.34 |

(3) Physicochemical Properties of Bovine Membrane-bound Sialidase

The physicochemical properties of the enzyme investigated by using the aforementioned purified enzyme are shown below.

(i) Substrate Specificity

The results of investigations about the activity of the enzyme of the present invention for various substrates are shown in Table 2. The numerical values represent relative activity when the activity for the GD3-ganglioside is defined to be 100.

TABLE 2

| Substrate | Hydrolysis activity (%) |
|---|---|
| Ganglioside | |
| GD3-ganglioside | 100 |
| GD1a-ganglioside | 56 |
| GM3-ganglioside | 62 |
| GM2-ganglioside | 3 |
| GM1-ganglioside | 1 |
| Synthetic ganglioside | |
| GSC-17 (α2–3) | 110 |
| GSC-61 (α2–6) | 44 |
| Orosomucoid | 2 |
| Fetuin | 2 |
| Glycophorin | 3 |
| Ovine submaxillary gland mucin | 3 |
| Bovine submaxillary gland mucin | 0 |
| α2–3 syalyllactose | 11 |
| 4-MUNeuAC | 25 |

The hydrolysis of GSC-17 (α2-3) occurred at a rate 2.5 times higher than that of the hydrolysys of GSC-61 (α2-6), and hence the enzyme is considered to be more likely to act on α2-3 linkage compared with α2-6 linkage. Further, since it did not act on α2-3 syalyllactose corresponding to the saccharide segment of the GM3 ganglioside, the ceramide segment is indispensable for a substrate.

(ii) Optimum pH
4.7 to 5.0

(iii) Molecular Weight

About 65,000 as determined by sucrose density gradient centrifugation,

About 52,000 as determined by SDS-polyacrylamide gel electrophoresis under reducing condition.

(iv) Inhibition, Activation etc.

A detergent is required for the activity. For example, it is highly active in the presence of 0.1 to 0.2% of Triton X-100.

Residual activities in the presence of various inhibitors are shown in Table 3. The numerical values each represent 100 minus (residual activity (%) in the presence of inhibitor).

TABLE 3

| Inhibitor | Inhibition (%) |
|---|---|
| CuCl$_2$(1 mM) | 95 |
| 4-Hydroxy mercury benzoate (50 μM) | 92 |
| 2-Deoxy-2,3-dehydro-N-acetylneuraminic acid (0.2 mM) | 45 |

(3) Peptide Sequencing

Because the above-obtained final product was obtained at a low yield, the enzyme fraction of Step 9 was prepared in a similar manner by using 6 kg of bovine brains as the starting material, and subjected to peptide analysis. The enzyme fraction was desalted by dialysis in the presence of 0.1% PVP-40 (Sigma), concentrated with Centricon (Millipore), subjected to SDS-polyacrylamide gel electrophoresis as described above, and transferred to a PVDF membrane (Problott, Applied Biosystems). The location of the enzymatic protein was confirmed by Ponceau S staining, and the corresponding part of the membrane was excised, and digested with lysyl endopeptidase and then with endoproteinase Asp-N. The product was separated by high performance liquid chromatography.

The fractionated peptide was subjected to amino acid sequencing using a peptide sequencer (Shimazu PSQ1). The above microsequencing was performed according to the method of Iwamatsu et al. (Iwamatsu A. and Yoshida-Kubomura N., *J. Biochem.* 120, 29–34, 1996). The obtained sequences are represented in FIG. 1 and SEQ ID NOS: 5–9. SEQ ID NOS: 5–7 are amino acid sequences of the fragments obtained by the endoproteinase digestion, and SEQ ID NOS: 8 and 9 are amino acid sequences of the fragments obtained by the lysyl endopeptidase digestion. In SEQ ID NO: 5, the 2–5th amino acids are indefinite, and it is highly possible that the 2nd amino acid should be Ala or Arg, the 3rd amino acid be Glu or Gly, the 4th amino acid be Ile or Tyr, and the 5th amino acid be Leu or Ser.

<2> cDNA Cloning of Bovine Brain Sialidase

Based on the amino acid sequence of the peptide of the purified enzyme, which had been determined as described above, 10 sense or antisense degenerate primers of SEQ ID NOS: 10 (DN1-1S), 11 (DN1-1A), 12 (DN1-2S), 13 (DN1-2A), 14 (DN2S), 15 (DN2A), 16 (DN3A), 17 (AP1A), 18 (AP3S), and 19 (AP3A) were prepared (see FIG. 1). DN1, DN2, DN-3, AP-1, and AP-3 are designations of the peptides shown in FIG. 1, S means "sense", and A means "antisense". DN-1 represents a nucleotide sequence determined by assuming that the undefinite amino acids of DN-1 (the 2–5th amino acids) should be Ala, Glu, Ile, and Leu, respectively, and DN-2 represents a nucleotide sequence determined by assuming that the undefinite amino acids of DN-1 should be Arg, Gly, Tyr, and Ser, respectively.

Bovine brain total RNA was prepared by the acid guanidium-phenol-chloroform method (Chomczynski P. and Sacchi N., *Anal. Biochem.* 162, 156–159, 1987), and poly (A) $^+$RNA was purified by oligo(dT)-cellulose column chromatography. cDNA was prepared in accordance with the previous report (Miyagi T. et al., *J. Biol. Chem.* 268, 26435–26440, 1993) using the poly(A) $^+$RNA (1 mg) and reverse transcriptase (derived from Molony murine leukemia virus, BRL), and amplification by PCR utilizing the cDNA as a template was attempted.

The PCR reaction mixture (50 ml) had a composition of 50 mM KCl, 10 mM Tris-HCl (pH 8.3), 1.5 mM $MgCl_2$, 0.01% of gelatin, 0.2 mM dNTPs (2 mM each of dATP, dGTP, dCTP and dTTP), 0.5 mg of cDNA, and 1.5 units of Taq polymerase (Ex Taq, Takara). The DNA amplification was performed by 40 cycles of reactions of at 94° C. (0.5 minutes), 50° C. (1 minute) and 72° C. (2 minutes), followed by extension reaction at 72° C. for 10 minutes. The obtained 12 DNA amplification fragments were each subcloned in the SmaI site of Bluescript vector (Stratagene), and subjected to DNA sequencing by the dideoxy method (Sanger F. et al., *Proc. Natl. Acad. Sci. USA*, 74, 5463–5467, 1977).

As a result of examination for the validity of the amino acid sequences deduced from the nucleotide sequences of the segments corresponding to the primers within the amplified DNA fragments, presence or absence of a stop codon and the like, it was found that only a PCR product of 0.5 kb obtained with primers AP3S and DN2A fulfilled those requirements. In addition, two Asp-boxes (-Ser-Xaa-Asp-Xaa-Gly-Xaa-Thr-Trp- (SEQ ID NO: 20)), which is a consensus sequence of sialidase, were found in this fragment (amino acid numbers 131–138 and 205–212 in SEQ ID NO: 2), and the deduced amino acid sequence exhibited 38% homology with respect to the amino acid sequence of the cytoplasmic sialidase, which we had previously isolated. However, it did not exhibit significant homology with any other proteins.

Then, a bovine brain λgt10 library (Clontech) was screened by using the above 0.5 kb cDNA as a probe. The cDNA was isotope-labeled with [α-$^{32}$P]dCTP using Random Primer DNA Labeling Kit (Takara), and phages (2×10$^6$) were screened by plaque hybridization. The hybridization was carried out by using a nylon membrane (Hybond N$^+$, Amersham) according to the instruction of the manufacturer. Among 15 positive clones, two of pBB121 (1.45 kb) and pBB321 (2.8 kb) were estimated to contain the full coding region.

The nucleotide sequence of the insert of pBB321 (2.8 kb) and the amino acid sequence deduced from it are shown as SEQ ID NOS: 1 and 2. It was found that four types of amino acid sequences obtained from the peptide of the purified product were contained in it, and as for DN-1, the 2nd amino acid of DN 1-1 was A R. Moreover, because it was found that the same sequence was contained in bovine keratin based on protein database search, although it was not found for the AP-1 sequence, it is highly possible that it originated from contamination of keratin in the enzyme fraction used for the peptide sequencing.

In addition to the above-mentioned two Asp-boxes, another Asp-box was further found on their 3' side (the amino acid numbers 256–263 in SEQ ID NO: 2). A hydrophobic sequence considered to be a transmembrane domain was found between the two Asp-boxes (the amino acid numbers 174–194 in SEQ ID NO: 2), and a glycosylation site was found on its 3' side (the amino acid number 349 in SEQ ID NO: 2). Because the enzyme has the characteristic that it is bound to RCA lectin as used in the purification procedure, it is considered that a saccharide chain actually attached to this site. The molecular weight of the protein calculated from the 428 amino acids is 48,000, and if one saccharide chain is attached, the actual value will become around 50,000, and it is not contradictory to the value determined for the above purified product by SDS-polyacrylamide gel electrophoresis.

<3> Transient Expression of Sialidase cDNA in COS Cell

The coding region of pBB121 (1.45 kb) was amplified by PCR using 5' sense primer (SEQ ID NO: 21) which was added an EcoRI site and 3' antisense primer (SEQ ID NO: 22), and the obtained DNA fragment was purified by agarose electrophoresis. This product was ligated to the EcoRI site of SRα promoter high expression vector pME18S (provided by Dr. Kazuo Maruyama, Medical Department, Tokyo Medical and Dental University) having SV40 replication origin (pME18S-mSD), and introduced into COS-7 cells by electroporation to attempt its transient expression. Forty μg of pME18S or pME18S-mSD was added to COS-7 cells (10$^6$) cultured in DMEM containing 10% FBS (fetal bovine serum) in the logarithmic growth phase, left at room temperature for 10 minutes, applied with electric pulses at 250 V and 950 μFD, left at room temperature again for 10 minutes, and then returned to the culture.

The cells after the culture of 48 hours were collected. After the blood serum components were removed with PBS, the cells were added 9 volumes of PBS, and disrupted by ultrasonication for 10 seconds. The disrupted cell suspension was centrifuged under cooling at 1,000×g for 10 minutes, and the resulting supernatant was used as a homogenate. Sialidase activity in the homogenate of the transfectants was measured by using gangliosides as the substrate in the presence of Triton X-100 (0.1%).

The specific activity of control cells having only the vector and the cells that were introduced with pME18S-mSD was 23.4 units/mg protein and 844.5 units/mg protein, respectively. Thus, the cells introduced with pME18S-mSD exhibited the activity 36 times higher than that of the control cells. However, increase of the activity for hydrolyzing 4MU-sialic acid was not observed at all. This result confirmed the results of the previous characterization of the purified product of the bovine brain enzyme, i.e., the expressed sialidase substantially specifically acted on gangliosides, and hardly acted on synthetic substrates such as 4MU-sialic acid.

Further, it was investigated whether the expressed sialidase localized in plasma membrane or not by using Percoll (Pharmacia) concentration gradient centrifugation. In accordance with a previous report (Sagawa J. et al., *J. Biochem.* 107, 452–456, 1990), the homogenate was overlaid on 40% Percoll containing 0.25 M sucrose, centrifuged at 48,000×g for 40 minutes, and fractionated, and the sialidase activity was measured. Ganglioside sialidase activity was detected at the same location as the activity distribution of 5'-nucleotidase or alkali phosphatase, which are marker enzymes of plasma membrane, and thus the localization of the expressed sialidase in plasma membrane was confirmed.

<4> cDNA Cloning of Human-derived Ganglioside Sialidase

When the primary structure of the bovine brain sialidase was compared with the previously isolated cytoplasmic sialidase (Miyagi T. et al., *J. Biol. Chem.*, 268, 26435–26440, 1993), it was found that they contained a sequence well conserved in them (FIG. 2). Therefore, one set of primers was prepared based on this amino acid sequence (SEQ ID NOS: 23 and 24). In the amino acid sequences shown in FIG. 2, the partial sequence of cDNA for bovine brain sialidase (BBmSD) corresponds to the amino acid numbers 49–209 of SEQ ID NO: 2. The rat skeletal muscle cytoplasmic sialidase (RMcSD) corresponds to the amino acid numbers 1–240 in the amino acid sequence of the sialidase.

Human brain cDNA and human kidney cDNA were prepared under the same condition as the case of the bovine enzyme, and PCR was performed by using them as the template. The amplified DNA fragment of 0.25 kb was subcloned, and the DNA sequence was determined. One Asp-box was found in this cDNA. A human brain λgt10 cDNA library and human kidney λgt10 cDNA library (Clontech) were screened by using the above DNA as a probe. By screening $8 \times 10^5$ plaques for human brain and $1 \times 10^6$ plaques for human kidney, three positive clones (pHB82, pHB85, and pHB95) and one positive clone (pHK65) were obtained, respectively.

When these DNA sequences were investigated after subcloning, an overlapped portion of 1 kb was found in all of them. Nucleotide sequences obtained from pHB95 containing the substantially whole coding region and pHK65 containing 3' end non-coding region of 1 kb, and deduced amino acid sequences therefor are shown as SEQ ID NOS: 3 and 4. They exhibited high homology with the sequences for bovine brain enzyme, i.e., 81% (87% for only the coding region) on the nucleotide level, and 82% on the amino acid level.

In SEQ ID NO: 4, the transmembrane domain corresponds to the amino acid numbers 174–194, the glycosylation site to the amino acid number 348, and the Asp-boxes to the amino acid numbers 131–138, 205–212, and 256–263.

When the expression status was investigated in various human tissues by Northern blotting using the 1.5 kb insert of pHB95 as the probe, high expression of mRNA of about 4 kb was observed in skeletal muscles, and mRNA of the same size was also detected in brain, liver and the like.

Industrial Availability

The present invention provides sialidase localized in plasma membrane and DNA coding for it. The sialidase of the present invention differs from sialidases known so far in that it mainly localizes in plasma membrane, and specifically hydrolyze gangliosides.

What is claimed is:

1. An isolated DNA encoding a protein comprising an amino acid sequence of SEQ ID NO: 2.

2. The DNA according to claim 1, wherein the protein includes substitution, deletion, or insertion of one or several amino acid residues, and exhibits activity to remove a sialic acid residue from a non-reducing terminal of ganglioside.

3. A vector comprising the DNA of claim 1.

4. An isolated DNA encoding for a protein comprising an amino acid sequence of SEQ ID NO: 4.

5. The DNA according to claim 4, wherein the protein includes substitution, deletion, or insertion of one or several amino acid residues, and exhibits activity to remove a sialic acid residue from a non-reducing terminal of ganglioside.

6. A vector comprising the DNA of claim 4.

7. The DNA according to claim 1 which has a nucleotide sequence of SEQ ID NO: 1.

8. The DNA according to claim 4 which has a nucleotide sequence of SEQ ID NO: 3.

9. A vector comprising the DNA of claim 7.

10. A vector comprising the DNA of claim 8.

* * * * *

SEQUENCE LISTING

```
<160> NUMBER OF SEQ ID NOS: 24

<210> SEQ ID NO 1
<211> LENGTH: 3003
<212> TYPE: DNA
<213> ORGANISM: Bos primigenius taurus
<220> FEATURE:
<221> NAME/KEY: CDS
<222> LOCATION: (259)..(1542)

<400> SEQUENCE: 1
ggagcttcct ggacttcctt tcctaacggc tgttttcggc ttccccaatc tgtcagcccc      60
gccgccagcc tctcgatgtc tctgtcgccg tgtttcttca cttttcgtgg tttgtgtccg     120
cgtccgcagt ttctctcctg ccctcgtctc cagggcttga tcattctcca gggcttcagt     180
gtcggagacg tgagtgcttg acccagcgcc cagatcagcc cgagagagat ggaggagccg     240
gggttccctg cagaggtc atg gaa gaa gtg aca tca tgc tcc ttc agc agc      291
                    Met Glu Glu Val Thr Ser Cys Ser Phe Ser Ser
                     1               5                      10 cct ctg ttc cag cag gag gac aag aga ggg gtc acc tac cgg atc cca      339
Pro Leu Phe Gln Gln Glu Asp Lys Arg Gly Val Thr Tyr Arg Ile Pro
            15                  20                  25 gcc ctg atc tac gtg ccc cct gcc cac acc ttc ctg gcc ttt gca gag      387
Ala Leu Ile Tyr Val Pro Pro Ala His Thr Phe Leu Ala Phe Ala Glu
        30                  35                  40
```

```
aag cgc tcc tcg agc aag gat gag gat gct ctc cac ctg gtg ctg agg        435
Lys Arg Ser Ser Ser Lys Asp Glu Asp Ala Leu His Leu Val Leu Arg
         45                  50                  55 cga gga tta agg act ggg caa tca gta cag tgg gaa ccc ctg aag tcc        483
Arg Gly Leu Arg Thr Gly Gln Ser Val Gln Trp Glu Pro Leu Lys Ser
 60                  65                  70                  75 ctg atg aaa gcc acg tta cct gga cac cgg acc atg aac ccc tgt cct        531
Leu Met Lys Ala Thr Leu Pro Gly His Arg Thr Met Asn Pro Cys Pro
                 80                  85                  90 gtg tgg gag cgg aag agt ggc tac gtg tac ctg ttc ttc atc tgt gtg        579
Val Trp Glu Arg Lys Ser Gly Tyr Val Tyr Leu Phe Phe Ile Cys Val
             95                 100                 105 caa ggc cat gtc acc gag cgt caa cag att atg tca ggc agg aac cct        627
Gln Gly His Val Thr Glu Arg Gln Gln Ile Met Ser Gly Arg Asn Pro
        110                 115                 120 gca cgc ctc tgc ttc ata tgc agc cag gat gct ggc tat tca tgg agt        675
Ala Arg Leu Cys Phe Ile Cys Ser Gln Asp Ala Gly Tyr Ser Trp Ser
    125                 130                 135 gat gtg agg gac ctg act gag gag gtc att ggc cca gag gtg aca cac        723
Asp Val Arg Asp Leu Thr Glu Glu Val Ile Gly Pro Glu Val Thr His
140                 145                 150                 155 tgg gcc act ttt gct gtg ggg cca ggt cat ggc atc cag ctg cag tcg        771
Trp Ala Thr Phe Ala Val Gly Pro Gly His Gly Ile Gln Leu Gln Ser
                160                 165                 170 ggg agg ctc atc atc cct gca tat gcc tac tac atc ccg ttc tgg ttc        819
Gly Arg Leu Ile Ile Pro Ala Tyr Ala Tyr Tyr Ile Pro Phe Trp Phe
            175                 180                 185 ttt tgc ttt cgg ctg cca tat aga gct agg cct cat tcc ctg atg atc        867
Phe Cys Phe Arg Leu Pro Tyr Arg Ala Arg Pro His Ser Leu Met Ile
        190                 195                 200 tat agc gat gac cta gga gcc aca tgg cac cat ggc agg ctt atc aag        915
Tyr Ser Asp Asp Leu Gly Ala Thr Trp His His Gly Arg Leu Ile Lys
    205                 210                 215 ccc atg gtg aca gtg gaa tgt gaa gtg gca gag gtg atc ggg aag gcc        963
Pro Met Val Thr Val Glu Cys Glu Val Ala Glu Val Ile Gly Lys Ala
220                 225                 230                 235 ggc cac cct gtg ctg tat tgc agt gcc cgg aca cca aac agg cac cgg       1011
Gly His Pro Val Leu Tyr Cys Ser Ala Arg Thr Pro Asn Arg His Arg
                240                 245                 250 gca gag gcc ctc agc att gac cat ggt gaa tgc ttt cag aaa cca gtc       1059
Ala Glu Ala Leu Ser Ile Asp His Gly Glu Cys Phe Gln Lys Pro Val
            255                 260                 265 ctg agc cat cag ctc tgt gag ccc cct cat ggc tgt caa ggc agt gtg       1107
Leu Ser His Gln Leu Cys Glu Pro Pro His Gly Cys Gln Gly Ser Val
        270                 275                 280 gtg agt ttc tgt ccc ctg gag atc cca ggt gga tgc cag gat ctt gct       1155
Val Ser Phe Cys Pro Leu Glu Ile Pro Gly Gly Cys Gln Asp Leu Ala
    285                 290                 295 ggc gaa gat gca cct gcc att cag cag agt cct ctg ctg tgc agc tca       1203
Gly Glu Asp Ala Pro Ala Ile Gln Gln Ser Pro Leu Leu Cys Ser Ser
300                 305                 310                 315 gtg aga cca gag ccg gaa gct gga acc ctg tca gaa tca tgg ctc ttg       1251
Val Arg Pro Glu Pro Glu Ala Gly Thr Leu Ser Glu Ser Trp Leu Leu
                320                 325                 330 tac tca cac cca acc aat aag aaa cgg agg gtc gat cta ggc atc tac       1299
Tyr Ser His Pro Thr Asn Lys Lys Arg Arg Val Asp Leu Gly Ile Tyr
            335                 340                 345 ctc aac cag agc ccc ttg gag gct gcc tgc tgg tcc cgc ccc tgg atc       1347
Leu Asn Gln Ser Pro Leu Glu Ala Ala Cys Trp Ser Arg Pro Trp Ile
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 350 |     |     |     | 355 |     |     |     | 360 |     |     |     |     |     |      |
| ttg | cac | tgc | ggg | ccc | tgt | ggg | tac | tct | gat | ttg | gct | gct | ctg | gag | aat | 1395 |
| Leu | His | Cys | Gly | Pro | Cys | Gly | Tyr | Ser | Asp | Leu | Ala | Ala | Leu | Glu | Asn |      |
|     | 365 |     |     |     |     | 370 |     |     |     |     | 375 |     |     |     |     |      |
| gag | ggc | ttg | ttt | ggg | tgt | ttg | ttt | gaa | tgt | ggg | acc | aag | cag | gag | tgt | 1443 |
| Glu | Gly | Leu | Phe | Gly | Cys | Leu | Phe | Glu | Cys | Gly | Thr | Lys | Gln | Glu | Cys |      |
| 380 |     |     |     |     | 385 |     |     |     |     | 390 |     |     |     |     | 395 |      |
| gag | cag | att | gcc | ttc | cgc | ctg | ttt | aca | gac | cga | gag | atc | ctg | agc | cac | 1491 |
| Glu | Gln | Ile | Ala | Phe | Arg | Leu | Phe | Thr | Asp | Arg | Glu | Ile | Leu | Ser | His |      |
|     |     |     | 400 |     |     |     |     | 405 |     |     |     |     | 410 |     |     |      |
| gtg | caa | ggg | gac | tgc | tcc | acc | cct | ggt | atg | aac | tct | gag | cca | agt | aaa | 1539 |
| Val | Gln | Gly | Asp | Cys | Ser | Thr | Pro | Gly | Met | Asn | Ser | Glu | Pro | Ser | Lys |      |
|     |     |     | 415 |     |     |     |     | 420 |     |     |     |     | 425 |     |     |      |

| | | |
|---|---|---|
| aag taattcgctt aggacccaac tttgcataga aggctaccgt agaaggcagt | | 1592 |
| Lys | | |

```
cacagccagg acagtggagg ccaggataac agaggttact gaagtctgca gagaaacaaa      1652
acacctaata ttctgctccc tacctgtttt cacttctcat tctccagaga acaaaatgaa      1712
catcttgcca tagctactgc attcaaaaga gcactgaacg gtgagctgag agactatgat      1772
gtcatcttgg ctcttccact ggcttgcttt gggaccttgg acatgtcacc tgtactctct      1832
gggcctcagg tctccatctg taaaaggaga gggtcggatc tctgatttct cttcttccca      1892
tccctaggaa aggcagtgtg cctgcatgcc ccctgatcag caagtcctgg ctgtatgtag      1952
gactcttatc tcaaaggcag gctccgcttt tcaaatgact tgccactcat ccaagtataa      2012
ggttacaagc aggtgtcata gcacaaagga agatgtaggt ggcctgtttt gttttttaata     2072
acaaaagcac ttcatccctt ctgattatgc acgaagctct acagactcac tgttctagag      2132
gaatcgggcc aagcagcaga attataggtc acttaccttc tccagcttta cagctctgct      2192
ccaccttttcc ttccttgtcc agaaagcatt acctctgaag gagaaaatga gatgctcaat     2252
gtcagtgatc ttcaataatg gtacttaatg tttctgctgg catgactcct atgagagatg      2312
aacttgaagt tcatttatta ggatagttat tgatgagaaa tgaacatggg ttaggacttc      2372
aaagcatcgg acaaaacttt ctgctattgc tgctctcaag gagttcacag tttagggggc      2432
tagaagaggg ataaaattga agaaaataaa tgtagctggg gggatagttt atagatattg      2492
ggctctaagt gggagtgata gtagctgctg atggtattat tttaattgta tcttaattgt      2552
gcctggagtc atctgcccca gaacttgtcc aagctgctgt ttgttttttct cagaatgttg     2612
ttttcactca gccttcttta atggagacag tcgtcaccat tcagaaggtc tctggactca     2672
aaaacctctg aatcaagcat atttgttcag acctactgaa atttggacca tctctactat      2732
tagtgaagtg tagagatgct tctttatcta atagatttgg gataaacttt gacattgctg      2792
gttctcagat gatagcagat ggttgctctt attttagatc atttcctcca taagccttttt     2852
actgtgacag atactcttat tgtgagagct acctttttttg tccctatttt tggaggataa     2912
tgccttaaac aggcagcagg taaatatatt tggtgctgag taatgaccct ggagagtaag      2972
tcgttgtcgt ggaacacagc ctagaaagtg g                                     3003
```

<210> SEQ ID NO 2
<211> LENGTH: 428
<212> TYPE: PRT
<213> ORGANISM: Bos primigenius

<400> SEQUENCE: 2

Met Glu Glu Val Thr Ser Cys Ser Phe Ser Ser Pro Leu Phe Gln Gln
 1               5                  10                  15

```
Glu Asp Lys Arg Gly Val Thr Tyr Arg Ile Pro Ala Leu Ile Tyr Val
            20                  25                  30
Pro Pro Ala His Thr Phe Leu Ala Phe Ala Glu Lys Arg Ser Ser Ser
            35                  40                  45
Lys Asp Glu Asp Ala Leu His Leu Val Leu Arg Arg Gly Leu Arg Thr
            50                  55              60
Gly Gln Ser Val Gln Trp Glu Pro Leu Lys Ser Leu Met Lys Ala Thr
 65                  70                  75                  80
Leu Pro Gly His Arg Thr Met Asn Pro Cys Pro Val Trp Glu Arg Lys
                85                  90                  95
Ser Gly Tyr Val Tyr Leu Phe Phe Ile Cys Val Gln Gly His Val Thr
                100                 105             110
Glu Arg Gln Gln Ile Met Ser Gly Arg Asn Pro Ala Arg Leu Cys Phe
            115                 120                 125
Ile Cys Ser Gln Asp Ala Gly Tyr Ser Trp Ser Asp Val Arg Asp Leu
            130                 135                 140
Thr Glu Glu Val Ile Gly Pro Glu Val Thr His Trp Ala Thr Phe Ala
145                 150                 155                 160
Val Gly Pro Gly His Gly Ile Gln Leu Gln Ser Gly Arg Leu Ile Ile
                165                 170                 175
Pro Ala Tyr Ala Tyr Ile Pro Phe Trp Phe Phe Cys Phe Arg Leu
                180                 185                 190
Pro Tyr Arg Ala Arg Pro His Ser Leu Met Ile Tyr Ser Asp Asp Leu
                195                 200                 205
Gly Ala Thr Trp His His Gly Arg Leu Ile Lys Pro Met Val Thr Val
                210                 215                 220
Glu Cys Glu Val Ala Glu Val Ile Gly Lys Ala Gly His Pro Val Leu
225                 230                 235                 240
Tyr Cys Ser Ala Arg Thr Pro Asn Arg His Arg Ala Glu Ala Leu Ser
                245                 250                 255
Ile Asp His Gly Glu Cys Phe Gln Lys Pro Val Leu Ser His Gln Leu
                260                 265                 270
Cys Glu Pro Pro His Gly Cys Gln Gly Ser Val Val Ser Phe Cys Pro
                275                 280                 285
Leu Glu Ile Pro Gly Gly Cys Gln Asp Leu Ala Gly Glu Asp Ala Pro
                290                 295                 300
Ala Ile Gln Gln Ser Pro Leu Leu Cys Ser Ser Val Arg Pro Glu Pro
305                 310                 315                 320
Glu Ala Gly Thr Leu Ser Glu Ser Trp Leu Leu Tyr Ser His Pro Thr
                325                 330                 335
Asn Lys Lys Arg Arg Val Asp Leu Gly Ile Tyr Leu Asn Gln Ser Pro
                340                 345                 350
Leu Glu Ala Ala Cys Trp Ser Arg Pro Trp Ile Leu His Cys Gly Pro
                355                 360                 365
Cys Gly Tyr Ser Asp Leu Ala Ala Leu Glu Asn Glu Gly Leu Phe Gly
                370                 375                 380
Cys Leu Phe Glu Cys Gly Thr Lys Gln Glu Cys Glu Gln Ile Ala Phe
385                 390                 395                 400
Arg Leu Phe Thr Asp Arg Glu Ile Leu Ser His Val Gln Gly Asp Cys
                405                 410                 415
Ser Thr Pro Gly Met Asn Ser Glu Pro Ser Lys Lys
                420                 425
```

```
<210> SEQ ID NO 3
<211> LENGTH: 1892
<212> TYPE: DNA
<213> ORGANISM: Homo sapiens
<220> FEATURE:
<221> NAME/KEY: CDS
<222> LOCATION: (11)..(1294)

<400> SEQUENCE: 3
```

| | | |
|---|---|---|
| tgcagaggtc atg gaa gaa gtg aca aca tgc tcc ttc aac agc cct ctg<br>           Met Glu Glu Val Thr Thr Cys Ser Phe Asn Ser Pro Leu<br>            1              5                 10 | | 49 |
| ttc cgg cag gaa gat gac aga ggg att acc tac cgg atc cca gcc ctg<br>Phe Arg Gln Glu Asp Asp Arg Gly Ile Thr Tyr Arg Ile Pro Ala Leu<br> 15                  20                 25 | | 97 |
| ctc tac ata ccc ccc acc cac acc ttc ctg gcc ttt gca gag aag cgt<br>Leu Tyr Ile Pro Pro Thr His Thr Phe Leu Ala Phe Ala Glu Lys Arg<br>    30                  35                40                 45 | | 145 |
| tcc acg agg aga gat gag gat gct ctc cac ctg gtg ctg agg cga ggg<br>Ser Thr Arg Arg Asp Glu Asp Ala Leu His Leu Val Leu Arg Arg Gly<br>           50                  55                60 | | 193 |
| ttg agg att ggg cag ttg gta cag tgg ggc ccc ctg aag cca ctg atg<br>Leu Arg Ile Gly Gln Leu Val Gln Trp Gly Pro Leu Lys Pro Leu Met<br> 65                  70                 75 | | 241 |
| gaa gcc aca cta ccg ggg cat cgg acc atg aac ccc tgt cct gta tgg<br>Glu Ala Thr Leu Pro Gly His Arg Thr Met Asn Pro Cys Pro Val Trp<br>    80                  85                90 | | 289 |
| gag cag aag agt ggt tgt gtg ttc ctg ttc ttc atc tgt gtg cgg ggc<br>Glu Gln Lys Ser Gly Cys Val Phe Leu Phe Phe Ile Cys Val Arg Gly<br>           95                 100              105 | | 337 |
| cat gtc aca gag cgt caa cag att gtg tca ggc agg aat gct gcc cgc<br>His Val Thr Glu Arg Gln Gln Ile Val Ser Gly Arg Asn Ala Ala Arg<br>110                 115                120               125 | | 385 |
| ctt tgc ttc atc tac agt cag gat gct gga tgt tca tgg agt gag gtg<br>Leu Cys Phe Ile Tyr Ser Gln Asp Ala Gly Cys Ser Trp Ser Glu Val<br>            130                 135                140 | | 433 |
| agg gac ttg act gag gag gtc att ggc tca gag ctg aag cac tgg gcc<br>Arg Asp Leu Thr Glu Glu Val Ile Gly Ser Glu Leu Lys His Trp Ala<br>               145                 150                155 | | 481 |
| aca ttt gct gtg ggc cca ggt cat ggc atc cag ctg cag tca ggg aga<br>Thr Phe Ala Val Gly Pro Gly His Gly Ile Gln Leu Gln Ser Gly Arg<br>           160                 165                170 | | 529 |
| ctg gtc atc cct gcg tat acc tac tac atc cct tcc tgg ttc ttt tgc<br>Leu Val Ile Pro Ala Tyr Thr Tyr Tyr Ile Pro Ser Trp Phe Phe Cys<br>    175                  180                185 | | 577 |
| ttc cag cta cca tgt aaa acc agg cct cat tct ctg atg atc tac agt<br>Phe Gln Leu Pro Cys Lys Thr Arg Pro His Ser Leu Met Ile Tyr Ser<br>190                 195                200               205 | | 625 |
| gat gac cta ggg gtc aca tgg cac cat ggt aga ctc att agg ccc atg<br>Asp Asp Leu Gly Val Thr Trp His His Gly Arg Leu Ile Arg Pro Met<br>            210                 215                220 | | 673 |
| gtt aca gta gaa tgt gaa gtg gca gag gtg act ggg agg gct ggc cac<br>Val Thr Val Glu Cys Glu Val Ala Glu Val Thr Gly Arg Ala Gly His<br>               225                 230                235 | | 721 |
| cct gtg cta tat tgc agt gcc cgg aca cca aac agg tgc cgg gca gag<br>Pro Val Leu Tyr Cys Ser Ala Arg Thr Pro Asn Arg Cys Arg Ala Glu<br>           240                 245                250 | | 769 |
| gcg ctc agc act gac cat ggt gaa ggc ttt cag aga ctg gcc ctg agt<br>Ala Leu Ser Thr Asp His Gly Glu Gly Phe Gln Arg Leu Ala Leu Ser<br>    255                  260                265 | | 817 |

-continued

| | | |
|---|---|---|
| cga cag ctc tgt gag ccc cca cat ggt tgc caa ggg agt gtg gta agt<br>Arg Gln Leu Cys Glu Pro Pro His Gly Cys Gln Gly Ser Val Val Ser<br>270                       275                   280               285 | 865 |
| ttc cgg ccc ctg gag atc cca cat agg tgc cag gac tct agc agc aaa<br>Phe Arg Pro Leu Glu Ile Pro His Arg Cys Gln Asp Ser Ser Ser Lys<br>                    290                   295                   300 | 913 |
| gat gca ccc acc att cag cag agc tct cca ggc agt tca ctg agg ctg<br>Asp Ala Pro Thr Ile Gln Gln Ser Ser Pro Gly Ser Ser Leu Arg Leu<br>305                       310                   315 | 961 |
| gag gag gaa gct gga aca ccg tca gaa tca tgg ctc ttg tac tca cac<br>Glu Glu Glu Ala Gly Thr Pro Ser Glu Ser Trp Leu Leu Tyr Ser His<br>        320                   325                   330 | 1009 |
| cca acc agt agg aaa cag agg gtt gac cta ggt atc tat ctc aac cag<br>Pro Thr Ser Arg Lys Gln Arg Val Asp Leu Gly Ile Tyr Leu Asn Gln<br>335                       340                   345 | 1057 |
| acc ccc ttg gag gct gcc tgc tgg tcc cgc ccc tgg atc ttg cac tgt<br>Thr Pro Leu Glu Ala Ala Cys Trp Ser Arg Pro Trp Ile Leu His Cys<br>350                       355                   360               365 | 1105 |
| ggg ccc tgt ggc tac tct gat ctg gct gct ctg gag gag gag ggc ttg<br>Gly Pro Cys Gly Tyr Ser Asp Leu Ala Ala Leu Glu Glu Glu Gly Leu<br>                    370                   375                   380 | 1153 |
| ttt ggg tgt ttg ttt gaa tgt ggg acc aag caa gag tgt gag cag att<br>Phe Gly Cys Leu Phe Glu Cys Gly Thr Lys Gln Glu Cys Glu Gln Ile<br>                 385                   390                   395 | 1201 |
| gcc ttc cgc ctg ttt aca cac cgg gag atc ctg agt cac ctg cag ggg<br>Ala Phe Arg Leu Phe Thr His Arg Glu Ile Leu Ser His Leu Gln Gly<br>400                       405                   410 | 1249 |
| gac tgc acc agc cct ggt agg aac cca agc caa ttc aaa agc aat<br>Asp Cys Thr Ser Pro Gly Arg Asn Pro Ser Gln Phe Lys Ser Asn<br>        415                   420                   425 | 1294 |
| taattggctt aggacccaat ttccatagat gcaaatggca gttacagaca ggttaacaga | 1354 |
| agctactgaa gtctacagat aatcaaaaaa cttaatattc tgttccctac cttttttcac | 1414 |
| ttttcctcct ccaaagagca aaatgaaaat tttgccttag ctactgcagt ggaaagagca | 1474 |
| ctgaactagg agttggaaga caaggatgtg gtcctggctc tgcactggct tgcttttgga | 1534 |
| ccttggatgt gtcacctgaa ctctctggac ctcaggtttc catctgtaaa atgagagtat | 1594 |
| tggttctaag atttctcatc ttctcatccc taggacaagc atagtgcctg catgcttcat | 1654 |
| gatcagtaag tcctggctgc ataaaggact ctgatgtcaa aatggaaacc aggggactta | 1714 |
| ccttttcaca tgacttaccc ctcatccgag tgtgaggtta caagcaggtg tcatggcagg | 1774 |
| aaggaagacc agatctgtat gatttgttcc atttttaata acaaaaatat ccacacccct | 1834 |
| ttaataatgc tcagagttct gtaggctctc tatcctagag gaattgagca aaacagcc | 1892 |

<210> SEQ ID NO 4
<211> LENGTH: 428
<212> TYPE: PRT
<213> ORGANISM: Homo sapiens

<400> SEQUENCE: 4

Met Glu Glu Val Thr Thr Cys Ser Phe Asn Ser Pro Leu Phe Arg Gln
1                 5                   10                   15

Glu Asp Asp Arg Gly Ile Thr Tyr Arg Ile Pro Ala Leu Leu Tyr Ile
                  20                   25                   30

Pro Pro Thr His Thr Phe Leu Ala Phe Ala Glu Lys Arg Ser Thr Arg
        35                   40                   45

Arg Asp Glu Asp Ala Leu His Leu Val Leu Arg Arg Gly Leu Arg Ile
50                       55                   60

-continued

Gly Gln Leu Val Gln Trp Gly Pro Leu Lys Pro Leu Met Glu Ala Thr
 65                  70                  75                  80

Leu Pro Gly His Arg Thr Met Asn Pro Cys Pro Val Trp Glu Gln Lys
                 85                  90                  95

Ser Gly Cys Val Phe Leu Phe Ile Cys Val Arg Gly His Val Thr
            100                 105                 110

Glu Arg Gln Gln Ile Val Ser Gly Arg Asn Ala Ala Arg Leu Cys Phe
            115                 120                 125

Ile Tyr Ser Gln Asp Ala Gly Cys Ser Trp Ser Glu Val Arg Asp Leu
            130                 135                 140

Thr Glu Glu Val Ile Gly Ser Glu Leu Lys His Trp Ala Thr Phe Ala
145                 150                 155                 160

Val Gly Pro Gly His Gly Ile Gln Leu Gln Ser Gly Arg Leu Val Ile
                165                 170                 175

Pro Ala Tyr Thr Tyr Tyr Ile Pro Ser Trp Phe Phe Cys Phe Gln Leu
            180                 185                 190

Pro Cys Lys Thr Arg Pro His Ser Leu Met Ile Tyr Ser Asp Asp Leu
            195                 200                 205

Gly Val Thr Trp His His Gly Arg Leu Ile Arg Pro Met Val Thr Val
            210                 215                 220

Glu Cys Glu Val Ala Glu Val Thr Gly Arg Ala Gly His Pro Val Leu
225                 230                 235                 240

Tyr Cys Ser Ala Arg Thr Pro Asn Arg Cys Arg Ala Glu Ala Leu Ser
                245                 250                 255

Thr Asp His Gly Glu Gly Phe Gln Arg Leu Ala Leu Ser Arg Gln Leu
            260                 265                 270

Cys Glu Pro Pro His Gly Cys Gln Gly Ser Val Val Ser Phe Arg Pro
            275                 280                 285

Leu Glu Ile Pro His Arg Cys Gln Asp Ser Ser Lys Asp Ala Pro
            290                 295                 300

Thr Ile Gln Gln Ser Ser Pro Gly Ser Ser Leu Arg Leu Glu Glu
305                 310                 315                 320

Ala Gly Thr Pro Ser Glu Ser Trp Leu Leu Tyr Ser His Pro Thr Ser
                325                 330                 335

Arg Lys Gln Arg Val Asp Leu Gly Ile Tyr Leu Asn Gln Thr Pro Leu
                340                 345                 350

Glu Ala Ala Cys Trp Ser Arg Pro Trp Ile Leu His Cys Gly Pro Cys
            355                 360                 365

Gly Tyr Ser Asp Leu Ala Ala Leu Glu Glu Glu Gly Leu Phe Gly Cys
370                 375                 380

Leu Phe Glu Cys Gly Thr Lys Gln Glu Cys Glu Gln Ile Ala Phe Arg
385                 390                 395                 400

Leu Phe Thr His Arg Glu Ile Leu Ser His Leu Gln Gly Asp Cys Thr
                405                 410                 415

Ser Pro Gly Arg Asn Pro Ser Gln Phe Lys Ser Asn
            420                 425

<210> SEQ ID NO 5
<211> LENGTH: 10
<212> TYPE: PRT
<213> ORGANISM: Bos primigenius taurus
<220> FEATURE:
<221> NAME/KEY: UNSURE
<222> LOCATION: (2)
<223> OTHER INFORMATION: Xaa=ala or arg -continued

```
<220> FEATURE:
<221> NAME/KEY: UNSURE
<222> LOCATION: (3)
<223> OTHER INFORMATION: Xaa=glu or gly
<220> FEATURE:
<221> NAME/KEY: UNSURE
<222> LOCATION: (4)
<223> OTHER INFORMATION: Xaa=ile or tyr
<220> FEATURE:
<221> NAME/KEY: UNSURE
<222> LOCATION: (5)
<223> OTHER INFORMATION: Xaa=leu or ser

<400> SEQUENCE: 5

Asp Xaa Xaa Xaa Xaa Ser His Val Gln Gly
 1               5                  10

<210> SEQ ID NO 6
<211> LENGTH: 5
<212> TYPE: PRT
<213> ORGANISM: Bos primigenius taurus

<400> SEQUENCE: 6

Asp Asp Leu Gly Ala
 1               5

<210> SEQ ID NO 7
<211> LENGTH: 5
<212> TYPE: PRT
<213> ORGANISM: Bos primigenius taurus

<400> SEQUENCE: 7

Glu Glu Val Thr Ser
 1               5

<210> SEQ ID NO 8
<211> LENGTH: 5
<212> TYPE: PRT
<213> ORGANISM: Bos primigenius taurus

<400> SEQUENCE: 8

Lys Tyr Glu Glu Leu
 1               5

<210> SEQ ID NO 9
<211> LENGTH: 9
<212> TYPE: PRT
<213> ORGANISM: Bos primigenius taurus

<400> SEQUENCE: 9

Lys Asp Glu Asp Ala Leu His Leu Val
 1               5

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (6,15,17,18,24)
<223> OTHER INFORMATION: n=inosine

<400> SEQUENCE: 10
gaygcngara tyctnwnnca ygtnca                                          26
```

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (6,12,13,15,24)
<223> OTHER INFORMATION: n=inosine

<400> SEQUENCE: 11
ccctgnacrt gnnwnagrat tycngcrtc                                        29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (4,6,9,13,15,17,18,24)
<223> OTHER INFORMATION: n=inosine

<400> SEQUENCE: 12
gayngnggnt aynsnwnnca ygtncaggg                                        29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (6,11,12,14,16,21,24,26)
<223> OTHER INFORMATION: n=inosine

<400> SEQUENCE: 13
ccctgnacrt gnnwnsnrta nccncnrtc                                        29

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (9,11)
<223> OTHER INFORMATION: n=inosine

<400> SEQUENCE: 14
gaygayctng gngc                                                        14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (3,6)

<223> OTHER INFORMATION: n=inosine

<400> SEQUENCE: 15
gcnccnagrt crtc         14

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (1,3,4,7)
<223> OTHER INFORMATION: n=inosine

<400> SEQUENCE: 16
nsnngtnacy tcytc        15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (1,3)
<223> OTHER INFORMATION: n=inosine

<400> SEQUENCE: 17
nanytcytcr taytt        15

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (15,18,24)
<223> OTHER INFORMATION: n=inosine

<400> SEQUENCE: 18
aargaygarg aygcnctnca yctngt        26

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:synthetic
      oligonucleotide
<220> FEATURE:
<221> NAME/KEY: unsure
<222> LOCATION: (3,9,11)
<223> OTHER INFORMATION: n=inosine

<400> SEQUENCE: 19
acnagrtgna gngcrtcytc rtc        23

<210> SEQ ID NO 20
<211> LENGTH: 8
<212> TYPE: PRT
<213> ORGANISM: Unknown

```
<220> FEATURE:
<223> OTHER INFORMATION: Description of Unknown Organism:consensus
      sequence
<220> FEATURE:
<221> NAME/KEY: UNSURE
<222> LOCATION: (2,4,6)
<223> OTHER INFORMATION: Xaa=optional amino acid

<400> SEQUENCE: 20

Ser Xaa Asp Xaa Gly Xaa Thr Trp
  1               5

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 21
cccgaattcg tcatggaaga agtgacatca                                      30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 22
cccgaattct tactttttac ttggctcaga                                      30

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 23
ggacaccgga ccatgaaccc ctgtcct                                         27

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 24
cctggcccca cagcaaaagt ggccca                                          26
```